US005703016A

United States Patent [19]

Magin et al.

[11] Patent Number: 5,703,016
[45] Date of Patent: Dec. 30, 1997

[54] SURFACTANT COMPOSITION FOR USE WITH GLYPHOSATE COMPRISING DIMETHYL AMINE OXIDE, POLYETHOXYLATED ALCOHOL, AND PYRIDINIUM HALIDE

[75] Inventors: Ralph W. Magin; Joe D. Sauer, both of Baton Rouge, La.

[73] Assignee: Albemarle Corporation, Richmond, Va.

[21] Appl. No.: 720,519

[22] Filed: Sep. 30, 1996

[51] Int. Cl.$^6$ .......... A01N 25/30; A01N 57/02; B01F 17/32; B01F 17/42; B01F 17/16
[52] U.S. Cl. .......... 504/206; 252/357
[58] Field of Search .......... 504/206, 116; 252/357

[56] References Cited

U.S. PATENT DOCUMENTS

| | | | |
|---|---|---|---|
| 4,075,002 | 2/1978 | Drewe et al. | 71/92 |
| 4,159,901 | 7/1979 | Beestman et al. | 71/86 |
| 4,400,196 | 8/1983 | Albrecht et al. | 71/86 |
| 4,475,942 | 10/1984 | Bakel | 71/86 |
| 4,481,026 | 11/1984 | Prisbylla | 71/86 |
| 4,844,734 | 7/1989 | Iwasaki et al. | 71/120 |
| 4,931,080 | 6/1990 | Chan et al. | 71/87 |
| 5,047,079 | 9/1991 | Djafar et al. | 71/86 |
| 5,258,359 | 11/1993 | Kassebaum et al. | 504/206 |
| 5,317,003 | 5/1994 | Kassebaum et al. | 504/116 |
| 5,324,708 | 6/1994 | Moreno et al. | 504/206 |
| 5,464,806 | 11/1995 | Kassebaum et al. | 504/206 |
| 5,464,807 | 11/1995 | Claude et al. | 504/206 |

FOREIGN PATENT DOCUMENTS

| | | |
|---|---|---|
| 0274369 | 7/1988 | European Pat. Off. |
| 0483095 | 4/1992 | European Pat. Off. |
| 0498785 | 8/1992 | European Pat. Off. |
| 0577914 | 1/1994 | European Pat. Off. |
| 0617894 | 10/1994 | European Pat. Off. |
| 8704595 | 8/1987 | WIPO |
| 9516351 | 6/1995 | WIPO |
| 9600010 | 1/1996 | WIPO |

OTHER PUBLICATIONS

Wyrill, III, J. B. and Burnside, O.C.—"Glyphosate Toxicity to Common Milkweed and Hemp Dogbane as Influenced by Surfactants", Weed Science, vol. 25 Issue 3 (May), 1977, pp. 275–287.

*Primary Examiner*—S. Mark Clardy
*Attorney, Agent, or Firm*—Philip M. Pippenger

[57] ABSTRACT

Glyphosate formulations which are effective even when employed at dosages below the dosage currently recommended for post-emergent herbicidal or plant growth regulant use are described. They are formulated as water solutions or powders or granules from (a) one or more agriculturally acceptable salts of glyphosate; (b) at least one water-soluble long chain aliphatic hydrocarbyl dimethyl amine oxide in which the hydrocarbyl group is a linear or substantially linear saturated or olefinically unsaturated aliphatic group having in the range of about 8 to about 22 carbon atoms; (c) at least one water-soluble straight or branched chain saturated or olefinically unsaturated alcohol ethoxylate having in the range of about 8 to about 24 carbon atoms in the aliphatic hydrocarbyl group and in the range of about 2 to about 50 ethyleneoxy groups per molecule, and (d) at least one water-soluble or water-dispersible N-hydrocarbyl pyridinium halide having up to about 24 carbon atoms in the molecule, and wherein (i) the hydrocarbyl group attached to the nitrogen atom of the heterocyclic aromatic ring of the pyridinium nucleus is a saturated or olefinically unsaturated aliphatic hydrocarbyl group having in the range of about 4 to about 18 carbon atoms, and (ii) the ring carbon atoms of the pyridinium nucleus itself are either unsubstituted or one or more of such ring carbon atoms are substituted with a short chain alkyl group of up to about 4 carbon atoms, or a solution or suspension thereof.

35 Claims, No Drawings

SURFACTANT COMPOSITION FOR USE WITH GLYPHOSATE COMPRISING DIMETHYL AMINE OXIDE, POLYETHOXYLATED ALCOHOL, AND PYRIDINIUM HALIDE

TECHNICAL FIELD

This invention relates to glyphosate formulations which are highly effective even when employed at dosages below the dosage currently recommended for post-emergent herbicidal use against undesired vegetation.

BACKGROUND

Glyphosate, N-(phosphonomethyl)glycine, is a well-known widely used herbicide. It is generally employed in the form of an agriculturally acceptable salt.

In U.S. Pat. No. 5,116,401 to D. C. Young it is pointed out that although glyphosate is a very active, broad spectrum, systemic, relatively environmentally safe herbicide, its solubility in water at 25° C. is only 1.2 weight percent and many of its homologs and salts are only slightly soluble or are essentially insoluble in water and organic solvents. Thus in practice, formulations of glyphosate salts with other components to enhance its solubility and its effectiveness are typically used.

Over the years a wide variety of substances, including surfactants, have been studied or proposed as adjuvants to enhance the effectiveness of glyphosate. For example, J. W. Kassebaum and H. C. Berk indicate in U.S. Pat. No. 5,317,003, that surfactants are usually employed to enhance the effectiveness of glyphosate when it is applied to the foliage of various plants, and that the most widely used surfactant in commercial compositions is an ethoxylated fatty amine. In addition, they refer to knowledge in the art that a particular surfactant used in an aqueous composition with a herbicide can enhance the effectiveness of the herbicide, whereas other surfactants have very little, if any, beneficial effect. They also note that some surfactants may exhibit antagonistic effects. As an example they cite the work of Wyrill and Burnside, *Weed Science*, Volume 25, (1977), pages 275–287 wherein, among other things, it was found that the surfactant ETHOQUAD 18/12 was relatively ineffective in enhancing phytotoxicity of glyphosate to hemp dogbane whereas in a separate experiment an analogous compound, ETHOQUAD 18/25, was one of the most effective surfactants tested.

Despite the extensive studies and efforts devoted to improving the performance of glyphosate, a need exists for a way of potentiating the effectiveness of glyphosate salts such as the amine, ammonium, sodium, alkylsulfonium, alkylphosphonium, sulfonylamine, and aminoguanidine salts thereof by means of an environmentally friendly aqueous formulation made from a small number of ingredients, wherein the mounts of each of the components, including the glyphosate, can be kept very small, and wherein the resulting composition provides clearly observable herbicidal action, especially against broadleaf vegetation, in a short period of time after application. It would be particularly desirable if this need could be fulfilled by use of readily available, cost-effective materials while at the same time avoiding the inclusion of polyvalent metal-containing and metalloid-containing components in the formulation.

This invention is deemed to fulfill the foregoing need in an effective and highly efficient manner.

THE INVENTION

This invention involves the discovery, inter alia, that certain ternary combinations of tertiary amine oxides, alcohol ethoxylates and pyridinium halides are highly effective as co-adjuvants for increasing the phytotoxic effectiveness of glyphosate against common plant species. Thus this invention makes it possible to achieve enhanced phytotoxic effectiveness in an aqueous solution formed from as few as four added ingredients, all of which are readily available in the marketplace. Moreover it is possible pursuant to this invention to employ the glyphosate herbicide in dosage levels lower than currently recommended. Also, in many cases the co-adjuvants make it possible to bring about substantial reductions in glyphosate dosage levels while each of them is used at still smaller dosage levels than required if only one of the adjuvants is used without the others. Moreover, the adjuvants used in the practice of this invention are in themselves environmentally friendly. Further, the formulation requires no polyvalent metal or metalloid components in its formation. Indeed the preferred compositions are devoid of metal and metalloid additive content, and most preferably contain only the elements C, H, O, N, P, and Cl or Br, and optionally S. Moreover, the liquid concentrates are most preferably formed using deionized water.

The co-adjuvants used in forming the formulations of this invention are:

(1) one or more water-soluble or water-dispersible long chain aliphatic hydrocarbyl dimethyl amine oxides in which the hydrocarbyl group is a linear or substantially linear saturated or olefinically unsaturated aliphatic group having in the range of about 8 to about 22 carbon atoms, (2) one or more water-soluble or water-dispersible polyethoxylated monohydric saturated or olefinically-unsaturated alcohols of the formula:

$$RO-[CH_2CH_2O]_nH$$

in which R has at least about 8 carbon atoms and is a straight or branched chain saturated aliphatic hydrocarbyl group or a straight or branched chain monoolefinically or a polyolefinically unsaturated hydrocarbyl group having from 1 to 3 olefinic double bonds, and in which n is in the range of about 2 to about 50, or if a mixture, n is an average number in the range of about 2 to about 50, and (3) one or more water-soluble or water-dispersible N-hydrocarbyl pyridinium halides having up to about 24 carbon atoms in the molecule, and wherein (i) the hydrocarbyl group attached to the nitrogen atom of the heterocyclic aromatic ring of the pyridinium nucleus is a saturated or olefinically unsaturated aliphatic hydrocarbyl group having in the range of about 4 to about 18 carbon atoms, and (ii) the ring carbon atoms of the pyridinium nucleus itself are either unsubstituted or one or more of such ring carbon atoms are substituted with a short chain alkyl group of up to about 4 carbon atoms.

In one embodiment of this invention, a surfactant composition formed from these three, ingredients is provided.

By water-soluble is meant that the ingredient is soluble to at least the extent of 1% by weight in deionized water at 25° C. When used in forming an aqueous concentrate of this invention, the adjuvant should have a water solubility of at least 5% by weight in deionized water at 25° C. By water-dispersible is meant that if the ingredient is not soluble to the extent of 1% by weight in deionized water at 25° C., the amount of that ingredient in the form of particles no larger than 50 microns (preferably in the range of 10 to 30 microns) not dissolved when stirred for 5 minutes at 1000 rpm will remain suspended in the deionized water at 25° C. for at least 8 hours when 1% by weight of the other two ingredients of the ternary mixture when in the form of water-soluble ingredients are dissolved in the deionized water at 25° C.

In the practice of this invention, these co-adjuvants are typically employed in a weight ratios such that for every part by weight of (3) above, there are in the range of about 0.1 to about 10 parts by weight of (1) above, and in the range of about 0.1 to about 10 parts by weight of (2) above, and preferably in the range of about 0.2 to about 5 parts by weight of (1) above, and in the range of about 0.2 to about 5 parts by weight of (2) above, per each part by weight of (3) above. From a cost-effectiveness standpoint, a weight ratio of (1):(2):(3) in the range of 1.5–2.5:1.5–2.5:1, respectively, is especially desirable for providing rapid control of broadleaf weed species.

Pursuant to one of its embodiments this invention provides a method of controlling vegetation by applying to plant foliage, preferably by spraying, an effective herbicidal or growth regulant mount of a composition (preferably a polyvalent metal-free and metalloid-free composition) formed by mixing the following ingredients with water concurrently and/or in any sequence and/or in any preformed combination and/or subcombination thereof:

a) at least one agriculturally acceptable salt of glyphosate, or a solution or suspension thereof;

b) at least one water-soluble or water-dispersible long chain aliphatic hydrocarbyl dimethyl amine oxide in which the hydrocarbyl group is a linear or substantially linear saturated or olefinically unsaturated aliphatic group having in the range of about 8 to about 22 carbon atoms, or a solution or suspension thereof;

c) at least one water-soluble or water-dispersible polyethoxylated monohydric saturated or olefinically-unsaturated alcohol of the formula:

RO—[CH$_2$CH$_2$O]$_n$H in which R has at least about 8 carbon atoms and is a straight or branched chain saturated aliphatic hydrocarbyl group or a straight or branched chain monoolefinically or a polyolefinically unsaturated hydrocarbyl group having from 1 to 3 olefinic double bonds, and in which n is in the range of about 2 to about 50, or a solution or suspension thereof; and d) at least one water-soluble or water-dispersible N-hydrocarbyl pyridinium halide having up to about 24 carbon atoms in the molecule, and wherein (i) the hydrocarbyl group attached to the nitrogen atom of the heterocyclic aromatic ring of the pyridinium nucleus is a saturated or olefinically unsaturated aliphatic hydrocarbyl group having in the range of about 4 to about 18 carbon atoms, and (ii) the ring carbon atoms of the pyridinium nucleus itself are either unsubstituted or one or more of such ring carbon atoms are substituted with a short chain alkyl group of up to about 4 carbon atoms, or a solution or suspension thereof.

Another embodiment is a composition which comprises a solution or suspension containing at least a herbicidal or plant growth regulating amount of a composition formed by mixing the above ingredients (a), (b), (c) and (d) with water concurrently and/or in any sequence and/or in any preformed combination and/or subcombination thereof. Still another embodiment is a composition which comprises a powder or granular mixture containing at least a herbicidally or plant growth regulating amount of a composition formed from a combination of the above ingredients (a), (b), (c) and (d) brought together concurrently and/or in any sequence and/or in any preformed combination and/or subcombination thereof. Such powder, extruded or granular compositions can be formed by dry mixing the above ingredients (a), (b), (c) and (d). Alternatively, the powder or granular compositions can be formed by evaporating to dryness (e.g., by spray drying, extrusion or pan granulation) a solution (or if necessary, a slurry) of ingredients (a), (b), (c) and (d) above. Application of the powder, extruded or granular formulations to vegetation as foliar dusts for effecting control of the vegetation constitutes another embodiment of this invention.

Optionally, one or more substances, most preferably that are not herbicides, or plant growth regulants, or surfactants, such as dyes, humectants, corrosion inhibitors, stickers, spreaders and thickeners, can be included as additional ingredients in the compositions of this invention.

It will be appreciated that to effect control of undesired plant vegetation pursuant to this invention, recourse may be had to herbicidal activity whereby undesired vegetation is killed and/or to plant growth regulant activity whereby the further growth of the vegetation is stunted, inhibited and/or slowed without actually killing all of the undesired vegetation treated with the composition.

The herbicidal (phytotoxic) and the plant growth regulant compositions of this invention include aqueous concentrates which can be shipped and stored until diluted with more water on site to produce the final solution for application to the foliage as by spraying. Likewise the herbicidal and the plant growth regulant compositions of this invention include the more dilute aqueous solutions for use in application to the foliage. These more dilute aqueous solutions are preferably formed simply by suitably diluting a concentrate of this invention with water (if a powder, extruded or granular concentrate) or with more water (if a liquid concentrate) to achieve the appropriate herbicidal or plant growth regulant dosage, but alternatively, can be formed on site by intimately mixing the separate ingredients or sub-combinations thereof with sufficient water on site to achieve the appropriate dosage. Use of the solid or liquid concentrates of this invention is preferable as it is a much simpler operation and minimizes the possibility of blending errors. Moreover, if desired, other components such as fertilizers, penetrants, spreaders, stickers, etc., as well as other pesticide formulations can be introduced into the final solution at the time the concentrate is blended with water to form the diluted solution for application to the foliage.

INGREDIENT (a)

The identities and methods for the preparation of the glyphosate ingredient of the formulations are well known and are reported in the literature. See for example, U.S. Pat. No. 3,799,758 to J. E. Franz which describes amine salts and ammonium, alkali metal salts of glyphosate, and the production of glyphosate by such methods as the phosphonomethylation of glycine, the reaction of ethyl glycinate with formaldehyde and diethylphosphite, and the oxidation of the corresponding aminophosphinic compounds. Another method involves conducting a Mannich reaction with phosphorous acid and formaldehyde on iminodiacetic acid followed by controlled oxidation to N-(phosphonomethyl) glycine. Typically the amine of the glyphosate amine salts has a molecular weight of less than 300. A preferred amine salt of glyphosate is a salt formed with isopropyl amine. Of the alkali metal salts of glyphosate, sodium is the preferred cation. Inasmuch as glyphosate has more than one replaceable hydrogen atom, either or both of mono- and dialkali metal salts of glyphosate can be formed and used. The alkylsulfonium salts of glyphosate are described for example in U.S. Pat. No. 4,315,765 to G. B. Large, and analogous procedures can be used for producing alkylphosphonium salts. Of the alkylsulfonium and alkylphosphonium salts, the trimethylsulfonium salt of glyphosate is preferred. Sulfonylamine and aminoguanidine salts of glyphosate which are also suitable for use pursuant to this invention are disclosed for example in EP-A-0 088 180. The patent literature contains numerous additional references to various other methods for the production of glyphosate. See for example U.S. Pat. Nos. 4,851,159; 4,898,972; 4,937,376; 4,952,723; 5,061,820; and 5,072,033 to Fields Jr. et al.; 5,023,369 to Fields, Jr.; 4,853,159 to Riley et. al; and 5,047,579 to Glowka et al., as well as relevant references cited in these patents. Fields, Jr. et al. U.S. Pat. No. 4,965,403 describes a process for producing the alkali metal salts of glyphosate. Aqueous solutions of glyphosate salts devoid of other adjuvants are commercially available from Monsanto Company and these solutions are suitable for use in forming the compositions of this invention.

INGREDIENT (b)

This component in the form added to the water or aqueous solution is one or more water-soluble long chain aliphatic hydrocarbyl dimethyl amine oxides in which the hydrocarbyl group is a linear or substantially linear saturated or olefinically unsaturated aliphatic group having in the range of about 8 to about 22 carbon atoms. Preferably the long chain group is an alkyl group, most preferably a straight chain primary or normal alkyl group. Of the alkyl dimethyl amine oxide adjuvants of this invention, those in which the alkyl group contains about 8 to about 16 carbon atoms are preferred, and those in which the alkyl group contains about 12 to about 14 carbon atoms are more preferred, especially where the alkyl group is linear. n-Dodecyl dimethyl amine oxide is particularly preferred. Where the long chain group is olefinically unsaturated it will usually contain up to three olefinic double bonds and in the range of about 12 to about 22 carbon atoms. Of the water-soluble long chain unsaturated aliphatic hydrocarbyl dimethyl amine oxides, those having about 12 to about 18 carbon atoms in a substantially straight chain are preferred. As noted above, this component can be a single compound or a combination or mixture of two or more compounds. A few examples of such compounds include n-octyl dimethyl amine oxide, n-nonyl dimethyl amine oxide, n-decyl dimethyl amine oxide, n-undecyl dimethyl amine oxide, n-dodecyl dimethyl amine oxide, n-tridecyl dimethyl amine oxide, n-tetradecyl dimethyl amine oxide, n-pentadecyl dimethyl amine oxide, n-hexadecyl dimethyl amine oxide, n-heptadecyl dimethyl amine oxide, n-octadecyl dimethyl amine oxide, n-nonadecyl dimethyl amine oxide, n-eicosyl dimethyl amine oxide, n-heneicosyl dimethyl amine oxide, n-docosyl dimethyl amine oxide, 8-methyl-1-nonyl dimethyl amine oxide, 2,7-dimethyl-1-octyl dimethyl amine oxide, 1-dec-9-enyl dimethyl amine oxide, 6-methyl-1-undec-9-enyl dimethyl amine oxide, 1-dodec-8-enyl dimethyl amine oxide, 1-octadec-9-enyl dimethyl amine oxide, and the water-soluble isomers, analogs and homologs of the foregoing.

INGREDIENT (c)

There are, in general, several types of water-soluble polyethoxylated monohydric saturated or olefinically-unsaturated alcohols which can be utilized in the practice of this invention. In one type, the compounds have a saturated straight chain aliphatic hydrocarbyl group having in the range of about 8 to about 24 carbon atoms (preferably in the range of about 10 to about 20 carbon atoms), and in the range of 2 to about 50 ethyleneoxy groups (preferably in the range of about 5 to about 20 ethyleneoxy groups) in the molecule. A second type is compounds having an unsaturated saturated straight chain aliphatic hydrocarbyl group having in the range of about 8 to about 24 carbon atoms (preferably in the range of about 10 to about 20 carbon atoms) where the unsaturation is exclusively from 1 to about 3 olefinic double bonds, and in the range of 2 to about 50 ethyleneoxy groups (preferably in the range of about 5 to about 20 ethyleneoxy groups) in the molecule. A third type is composed of compounds having a saturated branched chain aliphatic hydrocarbyl group with one or more branches in the chain, and having in the range of about 8 to about 24 carbon atoms (preferably in the range of about 10 to about 20 carbon atoms). This third type also has in the range of 2 to about 50 ethyleneoxy groups (preferably in the range of about 5 to about 20 ethyleneoxy groups) in the molecule. Particularly preferred compounds of the third type have a single branch in the 2-position of the alkyl group. A fourth group is composed of compounds having an unsaturated branched chain aliphatic hydrocarbyl group having in the range of about 8 to about 24 carbon atoms (preferably in the range of about 10 to about 20 carbon atoms) where the unsaturation is exclusively from 1 to about 3 olefinic double bonds, and in the range of 2 to about 50 ethyleneoxy groups (preferably in the range of about 5 to about 20 ethyleneoxy groups) in the molecule. Mixtures or combinations of two or more adjuvants from any one or more of the above four types can be used.

Methods for producing the above polyethoxylated alcohols used as component (c) in the practice of this invention are also well known and are reported in the literature. Typically they involve the ethoxylation the appropriate alcohol typically in the presence of a base. Suitable compounds of the above formulas are available as articles of commerce.

INGREDIENT (d)

Water-soluble or water-dispersible N-hydrocarbyl pyridinium halide having up to about 24 carbon atoms in the molecule, and methods for their synthesis are known and reported in the literature. For use in this invention the pyridinium halide preferably satisfies these criteria: (i) the hydrocarbyl group attached to the nitrogen atom of the heterocyclic aromatic ring of the pyridinium nucleus is a saturated or olefinically unsaturated aliphatic hydrocarbyl group having in the range of about 4 to about 18 carbon atoms, and (ii) the ring carbon atoms of the pyridinium nucleus itself are either unsubstituted (i.e., they carry only hydrogen atoms) or one or more of such ring carbon atoms are substituted with a short chain alkyl group of up to about 4 carbon atoms. Some examples of this ingredient are N-butyl pyridinium chloride, N-isobutyl pyridinium chloride, N-pentyl pyridinium chloride, N-hexyl pyridinium chloride, N-heptyl pyridinium chloride, N-octyl pyridinium chloride, N-isooctyl pyridinium chloride, N-decyl pyridinium chloride, N-dodecyl pyridinium chloride, N-tetradecyl pyridinium chloride, N-hexadecyl pyridinium chloride, N-octadecyl pyridinium chloride, N-pent-3-enyl pyridinium chloride, N-dec-9-enyl pyridinium chloride, N-dodec-6-enyl pyridinium chloride, N-oleyl pyridinium chloride, N-butyl pyridinium bromide, N-isobutyl pyridinium bromide, N-pentyl pyridinium bromide, N-octyl pyridinium bromide, N-decyl pyridinium bromide, N-dodecyl pyridinium bromide, N-2-ethylhexyl pyridinium bromide, N-dodecyl pyridinium iodide, and water-soluble isomers, analogs and homologs of the foregoing. N-dodecyl pyridinium bromide or chloride are especially preferred. Mixtures or combinations of two or more of these ingredients can be used.

The compositions of this invention can be formed using any one or more of ingredients (a), (b), (c) and (d) in neat form or in the form of a solution or suspension thereof. The liquid medium for such solutions or suspensions is typically water but can be any suitable liquid which (i) is, or forms residues (if any) that are, agriculturally and toxicologically acceptable, and (ii) does not materially interfere with or destroy the herbicidal or plant growth regulant effectiveness of the composition when applied to the plant species to be controlled. Thus alcohols, esters, ethers, etc., or mixtures of one or more such materials with or without water can be used for this purpose.

Table 1 sets forth general and preferred proportions for use in forming the liquid concentrate formulations of this invention. The percentages given in Table 1 are weight percentages, and represent weight percent of the total composition. The percentages for the glyphosate salt such as amine, ammonium, alkali metal, alkylsulfonium, alkylphosphonium, sulfonylamine, and/or aminoguanidine or other agriculturally acceptable salt ("Glyphosate Salt"). used in the practice of this invention as given in Table 1 are on an active ingredient basis and are in terms of glyphosate acid equivalent (i.e., the weight of the particular salt-forming portion of the product is excluded from the weight of the salt). Likewise the amount of any water or other solvent associated with the salt as received is excluded from consideration as regards the percentages of the Glyphosate Salt shown in the table.

TABLE 1

| Ingredient | General Range, wt % | Preferred Range, wt % |
|---|---|---|
| (a) Glyphosate Salt | 0.1 to 65% | 18 to 65% |
| (b) Amine oxide | 1 to 35% | 10 to 20% |
| (c) Alcohol ethoxylate | 1 to 35% | 10 to 20% |
| (d) Pyridinium halide | 1 to 35% | 5 to 10% |
| Other Ingredient(s) | 0 to 20% | 0 to 5% |
| Water | Balance to 100% | Balance to 100% |

Table 2 sets forth the proportions which can be used in forming the powder or granular compositions of this invention. As in Table 1, the percentages given in Table 2 are weight percentages on an active ingredient basis, and represent weight percent of the total composition. And as above, the percentages for the ("Glyphosate Salt") e.g., amine, ammonium, alkali metal, alkylsulfonium, alkylphosphonium, sulfonylamine, and/or aminoguanidine salt, used in the practice of this invention as given in Table 2 are in terms of glyphosate acid equivalent.

TABLE 2

| Ingredient | General Range, wt % | Preferred Range, wt % |
|---|---|---|
| (a) Glyphosate Salt | 10 to 98% | 75 to 98% |
| (b) Amine oxide | 1 to 85% | 1 to 40% |
| (c) Alcohol ethoxylate | 1 to 85% | 1 to 40% |
| (d) Pyridinium halide | 1 to 85% | 1 to 20% |
| Other Ingredient(s) | 0 to 20% | 0 to 5% |

The diluted solutions for application to the plant foliage are typically formed prior to application using a tank mixer, spray tank or similar apparatus. The dosage level of the composition applied to the plant foliage will depend to some extent upon the plant species being treated, and the prevailing weather conditions. Generally speaking, however, the amount applied will be a herbicidally effective amount falling within the range of about 50 to about 1250 grams of glyphosate (on an acid equivalent basis, i.e., excluding the weight of the cationic salt associated therewith) per hectare. In terms of ounces avoirdupois per acre this range corresponds (on the same acid equivalent basis) to about 0.7 to about 20 ounces of glyphosate per acre. In accordance with this invention it is preferred to employ a herbicidally effective amount (again on an acid equivalent basis) falling within the range of about 200 to about 830 grams of glyphosate per hectare which corresponds (on the same acid equivalent basis) to about 3 to about 12 ounces avoirdupois of glyphosate per acre, as this is generally sufficient to control most undesired plant species, is below the dosage currently recommended for herbicidal use of glyphosate formulations, and is thus more economical and environmentally friendly. On the basis of this disclosure and the new technology described herein, it is now possible to make departures from the foregoing ranges whenever such is deemed necessary or desirable in any given situation.

The powder or granular formulations of this invention may be mixed with a finely-divided solid diluent such as talc, gypsum, Fuller's earth, kaolin, kieselguhr, bentonite, dolomite, calcium carbonate, and powdered magnesia. They may also be formulated as dispersible powders or grains, and in this case it is desirable to include a wetting agent to facilitate the dispersion of powder or grains in the liquid carrier.

The following non-limiting Examples illustrate the practice and advantages of this invention.

EXAMPLES

Herbicide performance enhancing capabilities of the adjuvants of this invention were investigated by a group of greenhouse tests in which a composition of this invention was used in the control of morning-glory ("MG") and hemp sesbania ("HS"). The test formulations consisted of aqueous solutions made from (a) N-(phosphonomethyl)glycine isopropyl amine salt, Co) tetradecyldimethylamine oxide, (c) a mixture of ethoxylated lauryl, myristic and cetyl alcohols (with an average of about 9 ethylene oxide units per molecule) made from a commercial mixture of these three alcohols having a typical weight ratio, respectively, of ca. 66.3:26.6:7.1, (d) N-n-dodecylpyridinium bromide, and water. No other ingredient was employed in forming the test formulations.

The glyphosate used in forming these formulations was ROUND-UP® D-Pak from Monsanto, which is a 62.0% aqueous solution of the glyphosate isopropyl amine salt in water with no other component therein. The control formulation was an aqueous solution of N-(phosphonomethyl) glycine isopropyl amine salt and the commercial adjuvant INDUCE® (Helena Chemical Company) which, according to A Guide to Agricultural Spray Adjuvants Used in the United States, by T. L. Harvey, 1992–93 Edition, Thomson Publications, Fresno, Calif., page 33 is alkyl polyoxyalkane ether, free fatty acids and IPA, which is an adjuvant currently recommended for use in glyphosate formulations. The formulations of this invention and the control formulations were applied to the plant species at the rates of 250 and 500 grams of glyphosate acid equivalent ("a.e.") per hectare. Two sets of these solutions were used. One set was formed using adjuvant to glyphosate (acid equivalent basis) ratios of 1:2. In the other set the ratios were 1:4.

Table 3 summarizes the test results with respect to the percentage of dry weight of the treated plants after 21 days as compared to the dry weight of corresponding untreated plants.

Table 4 summarizes the test results with respect to the percentage of plant height of the treated plants after 21 days as compared to the height of corresponding untreated plants. The symbol ⊕ signifies that the test formulation of this invention gave results that statistically were equivalent to the results given by the control formulation at 95% confidence limits. The symbol ⊙ signifies that statistically the result was superior to that of the control formulation at 95% confidence limits.

TABLE 3

Control of Morning-Glory and Hemp Sesbania
Under Greenhouse Conditions

| Adjuvant/ Glyphosate (a.e.) Ratio | Glyphosate Dosage Rate, grams (a.e.) per Hectare | MG Biomass, % of Untreated Plants | HS Biomass, % of Untreated Plants |
|---|---|---|---|
| 1:2 | 250 | ⊕ | ⊕ |
| 1:4 | 250 | ⊙ | ⊕ |
| 1:2 | 500 | ⊕ | ⊕ |
| 1:4 | 500 | ⊕ | ⊕ |

TABLE 4

Control of Morning-Glory and Hemp Sesbania
Under Greenhouse Conditions

| Adjuvant/ Glyphosate (a.e.) Ratio | Glyphosate Dosage Rate, grams (a.e.) per Hectare | MG Plant Height, % of Untreated Plants | HS Plant Height, % of Untreated Plants |
|---|---|---|---|
| 1:2 | 250 | ⊕ | ⊙ |
| 1:4 | 250 | ⊕ | ⊕ |
| 1:2 | 500 | ⊕ | ⊕ |
| 1:4 | 500 | ⊕ | ⊙ |

Using a rating scale of 1 to 3 where the higher the number the greater the injury to the plant, the above glyphosate compositions when applied to hemp sesbania at a dosage rate (a.e.) of 250 grams per hectare gave the results shown in Table 5. At the dosage rate (a.e.) of 500 grams per hectare the effects of the respective compositions were about the same.

TABLE 5

Phytotoxic Effect Produced with Hemp Sesbania
in Two Days after Treatment

| Composition | Adjuvant/Glyphosate (a.e.) Ratio | Plant Injury Rating, Two Days after Treatment |
|---|---|---|
| Invention | 1:2 | 2.8 |
| Control | 1:2 | 1.8 |
| Invention | 1:4 | 2.8 |
| Control | 1:4 | 2.8 |

It is to be understood that chemical compounds referred to by chemical name or formula anywhere in the specification or claims hereof, whether referred to in the singular or plural, are identified as they exist prior to coming into contact with another substance referred to by chemical name or chemical type (e.g., a reactant, a solvent, a diluent, or etc.). As a result of such contacting one or more chemical changes or transformations such as solvolysis, ionization, complex formation, chemical reaction or the like, may take place, and such changes or transformations, if the result of conducting an operation or procedure in accordance with this disclosure, are within the scope and contemplation of this invention. Thus there is no requirement that any chemical compound must remain unchanged when mixed with another ingredient, substance or compound as long as the operation or procedure being used is in accordance with the plain and ordinary meaning of this specification using common sense and ordinary knowledge and skill of a person skilled in the art. Accordingly, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. The fact that the substance, component or ingredient may have lost its original identity through a chemical reaction or transformation during the course of such contacting, blending or mixing operations is thus wholly immaterial for an accurate understanding and appreciation of this disclosure and the claims thereof.

Each and every patent or other publication referred to in any portion of this specification is fully incorporated into this disclosure by reference as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A composition which comprises a solution or suspension containing at least a herbicidal or plant growth regulating amount of a composition formed by mixing the following ingredients with water concurrently and/or in any sequence and/or in any preformed combination and/or sub-combination thereof:

a) at least one agriculturally acceptable salt of glyphosate, or a solution or suspension thereof;

b) at least one water-soluble or water-dispersible long chain aliphatic hydrocarbyl dimethyl amine oxide in which the hydrocarbyl group is a linear or substantially linear saturated or olefinically unsaturated aliphatic group having in the range of about 8 to about 22, carbon atoms, or a solution or suspension thereof;

c) at least one water-soluble or water-dispersible polyethoxylated monohydric saturated or olefinically-unsaturated alcohol of the formula:

in which R has at least about 8 carbon atoms and is a straight or branched chain saturated aliphatic hydrocarbyl group or a straight or branched chain monoolefinically or a polyolefinically unsaturated hydrocarbyl group having from 1 to 3 olefinic double bonds, and in which n is in the range of about 2 to about 50, or a solution or suspension thereof; and d) at least one water-soluble or water-dispersible N-hydrocarbyl pyridinium halide having up to about 24 carbon atoms in the molecule, and wherein (i) the hydrocarbyl group attached to the nitrogen atom of the heterocyclic aromatic ring of the pyridinium nucleus is a saturated or olefinically unsaturated aliphatic hydrocarbyl group having in the range of about 4 to about 18 carbon atoms, and (ii) the ring carbon atoms of the pyridinium nucleus itself are either unsubstituted or one or more of such ring carbon atoms are substituted with a short chain alkyl group of up to about 4 carbon atoms, or a solution or suspension thereof.

2. A composition according to claim 1 wherein said ingredient a) before it is mixed with any other ingredient used in forming said composition is an amine or alkylsulfonium salt of glyphosate or a solution or suspension thereof.

3. A composition according to claim 1 wherein said ingredient a) before it is mixed with any other ingredient used in forming said composition is the isopropyl amine salt of glyphosate or a solution or suspension thereof.

4. A composition according to claim 1 wherein said ingredient a) is the only herbicide used in forming said composition.

5. A composition according to claim 1 wherein said ingredient b) before it is mixed with any other ingredient used in forming said composition is one or more alkyl dimethyl amine oxides in which the alkyl group contains about 8 to about 16 carbon atoms, or a solution or suspension thereof; wherein said ingredient c) before it is mixed with any other ingredient used in forming said composition is one or more polyethoxylated saturated straight chain aliphatic alcohols in which the hydrocarbyl group has in the range of about 10 to about 20 carbon atoms, and in which there is an average in the range of about 5 to about 20 ethyleneoxy groups in the molecule, or a solution or suspension thereof; and wherein said ingredient d) before it is mixed with any other ingredient used in forming said composition is one or more N-alkyl pyridinium chlorides or bromides in which the N-alkyl group has in the range of about 10 to about 18 carbon atoms and in which the ring carbon atoms of the pyridinium nucleus itself are unsubstituted, or a solution or suspension thereof.

6. A composition according to claim 1 wherein said ingredient a) before it is mixed with any other ingredient used in forming said composition is one or more amine or alkylsulfonium salts of glyphosate, or a solution or suspension thereof; wherein said ingredient b) before it is mixed with the water or with any other ingredient used in forming said composition is one or more alkyl dimethyl amine oxides in which the alkyl group contains in the range of about 12 to about 16 carbon atoms, or a solution or suspension thereof; wherein said ingredient c) before it is mixed with the water or with any other ingredient used in forming said composition is a mixture of lauryl and myristyl alcohol ethoxylates having an average in the range of about 6 to about 12 ethyleneoxy groups per molecule, or a solution or suspension thereof; and wherein said ingredient d) before it is mixed with the water or with any other ingredient used in forming said composition is one or more N-alkyl pyridinium chlorides or bromides in which the alkyl group is an n-alkyl group having in the range of about 10 to about 16 carbon atoms, or a solution or suspension thereof.

7. A composition according to claim 6 wherein said ingredient a) before it is mixed with the water or with any other ingredient used in forming said composition is the isopropyl amine salt of glyphosate, or a solution or suspension thereof.

8. A composition according to claim 1 wherein the solution contains only the elements C, H, O, N, P; and Cl or Br, and optionally S, and is formed using deionized water.

9. A composition according to claim 1 wherein said ingredient a) before it is mixed with water or any other ingredient used in forming said composition is an amine salt of glyphosate; wherein on an active ingredient basis the weight ratio of ingredients b), c) and d) used in forming said solution is such that for each part by weight of d) there are in the range of about 0.3 to about 3 parts by weight of b), and in the range of about 0.3 to about 3 parts by weight of c); and wherein said solution is an aqueous concentrate adapted for dilution with water before use.

10. A composition according to claim 1 wherein said ingredient a) before it is mixed with water or any other ingredient used in forming said composition is an amine salt of glyphosate; wherein on an active ingredient basis the weight ratio of ingredients b), c) and d) used in forming said solution is such that for each part by weight of d) there are in the range of about 0.3 to about 3 parts by weight of b), and in the range of about 0.3 to about 3 parts by weight of c); and wherein said solution is a dilute water solution adapted for direct application to at least one plant species.

11. A composition according to claim 1 wherein ingredient b) is tetradecyldimethylamine oxide, ingredient e) is a mixture of ethoxylated lauryl, myristic and cetyl alcohols with an average of about 9 ethylene oxide units per molecule, and ingredient d) is N-dodecylpyridinium bromide.

12. A composition which comprises a powder or granular mixture containing at least a herbicidally or plant growth regulating amount of a composition formed from a combination of the following ingredients brought together concurrently and/or in any sequence and/or in any preformed combination and/or subcombination thereof:

a) at least one agriculturally acceptable salt of glyphosate, or a solution or suspension thereof;

b) at least one water-soluble or water-dispersible long chain aliphatic hydrocarbyl dimethyl amine oxide in which the hydrocarbyl group is a linear or substantially linear saturated or olefinically unsaturated aliphatic group having in the range of about 8 to about 22 carbon atoms, or a solution or suspension thereof;

c) at least one water-soluble or water-dispersible polyethoxylated monohydric saturated or olefinically-unsaturated alcohol of the formula:

in which R has at least about 8 carbon atoms and is a straight or branched chain saturated aliphatic hydrocarbyl group or a straight or branched chain monoolefinically or a polyolefinically unsaturated hydrocarbyl group having from 1 to 3 olefinic double bonds, and in which n is in the range of about 2 to about 50, or a solution or suspension thereof; and d) at least one water-soluble or water-dispersible N-hydrocarbyl pyridinium halide having up to about 24 carbon atoms in the molecule, and wherein (i) the hydrocarbyl group attached to the nitrogen atom of the heterocyclic aromatic ring of the pyridinium nucleus is a saturated or olefinically unsaturated aliphatic hydrocarbyl group having in the range of about 4 to about 18 carbon atoms, and (ii) the ring carbon atoms of the pyridinium nucleus itself are either unsubstituted or one or more of such ring carbon atoms are substituted with a short chain alkyl group of up to about 4 carbon atoms, or a solution or suspension thereof.

13. A composition according to claim 12 wherein said ingredient a) before it is mixed with any other ingredient used in forming said composition is an amine or alkylsulfonium salt of glyphosate or a solution or suspension thereof.

14. A composition according to claim 12 wherein said ingredient a) before it is mixed with any other ingredient used in forming said composition is the isopropyl amine salt of glyphosate or a solution or suspension thereof.

15. A composition according to claim 12 wherein said ingredient a) is the only herbicide used in forming said composition.

16. A composition according to claim 12 wherein said ingredient b) before it is mixed with any other ingredient used in forming said composition is one or more alkyl dimethyl amine oxides in which the alkyl group contains about 8 to about 16 carbon atoms, or a solution or suspension thereof; wherein said ingredient c) before it is mixed with any other ingredient used in forming said composition is one or more polyethoxylated saturated straight chain aliphatic alcohols in which the hydrocarbyl group has in the range of about 10 to about 20 carbon atoms, and in which there is an average in the range of about 5 to about 20 ethyleneoxy groups in the molecule, or a solution or suspension thereof; and wherein said ingredient d) before it is mixed with any other ingredient used in forming said composition is one or more N-alkyl pyridinium chlorides or bromides in which the N-alkyl group has in the range of about 10 to about 18 carbon atoms and in which the ring carbon atoms of the pyridinium nucleus itself are unsubstituted, or a solution or suspension thereof.

17. A composition according to claim 12 wherein said ingredient a) before it is mixed with any other ingredient used in forming said composition is one or more amine or alkylsulfonium salts of glyphosate, or a solution or suspension thereof; wherein said ingredient b) before it is mixed with any other ingredient used in forming said composition is one or more alkyl dimethyl amine oxides in which the alkyl group contains in the range of about 12 to about 16 carbon atoms, or a solution or suspension thereof; wherein said ingredient c) before it is mixed with any other ingredient used in forming said composition is a mixture of lauryl and myristyl alcohol ethoxylates having an average in the range of about 6 to about 12 ethyleneoxy groups per molecule, or a solution or suspension thereof; and wherein said ingredient d) before it is mixed with any other ingredient used in forming said composition is one or more N-alkyl pyridinium chlorides or bromides in which the alkyl group is an n-alkyl group having in the range of about 10 to about 16 carbon atoms, or a solution or suspension thereof.

18. A composition according to claim 17 wherein said ingredient a) before it is mixed with any other ingredient used in forming said composition is the isopropyl amine salt of glyphosate, or a solution or suspension thereof.

19. A composition according to claim 12 wherein the composition contains only the elements C, H, O, N, P, and Cl or Br, and optionally S.

20. A composition according to claim 12 wherein ingredient b) is tetradecyldimethylamine oxide, ingredient c) is a mixture of ethoxylated lauryl, myristic and cetyl alcohols with an average of about 9 ethylene oxide units per molecule, and ingredient d) is N-dodecylpyridinium bromide.

21. A surfactant composition which comprises a composition formed from the following active ingredients:

1) at least one water-soluble or water-dispersible long chain aliphatic hydrocarbyl dimethyl amine oxide in which the hydrocarbyl group is a linear or substantially linear saturated or olefinically unsaturated aliphatic group having in the range of about 8 to about 22 carbon atoms, or a solution or suspension thereof;

2) at least one water-soluble or water-dispersible polyethoxylated monohydric saturated or olefinically-unsaturated alcohol of the formula:

RO—[CH$_2$CH$_2$O]$_n$H in which R has at least about 8 carbon atoms and is a straight or branched chain saturated aliphatic hydrocarbyl group or a straight or branched chain monoolefinically or a polyolefinically unsaturated hydrocarbyl group having from 1 to 3 olefinic double bonds, and in which n is in the range of about 2 to about 50, or a solution or suspension thereof; and 3) at least one water-soluble or water-dispersible N-hydrocarbyl pyridinium halide having up to about 24 carbon atoms in the molecule, and wherein (i) the hydrocarbyl group attached to the nitrogen atom of the heterocyclic aromatic ring of the pyridinium nucleus is a saturated or olefinically unsaturated aliphatic hydrocarbyl group having in the range of about 4 to about 18 carbon atoms, and (ii) the ring carbon atoms of the pyridinium nucleus itself are either unsubstituted or one or more of such ring carbon atoms are substituted with a short chain alkyl group of up to about 4 carbon atoms, or a solution or suspension thereof;

and wherein on an active ingredient basis the weight ratio of ingredients 1), 2) and 3) used in forming said composition is such that for each part by weight of 3) there are in the range of about 0.3 to about 3 parts by weight of 1), and in the range of about 0.3 to about 3 parts by weight of 2).

22. A composition according to claim 21 wherein ingredient 1) is tetradecyldimethylamine oxide, ingredient 2) is a mixture of ethoxylated lauryl, myristic and cetyl alcohols with an average of about 9 ethylene oxide units per molecule, and ingredient 3) is N-dodecylpyridinium bromide.

23. A method of controlling vegetation which comprises applying to plant foliage a herbicidal or growth regulant amount of a composition formed by mixing the following ingredients with water concurrently and/or in any sequence and/or in any preformed combination and/or subcombination thereof:

a) at least one agriculturally acceptable salt of glyphosate, or a solution or suspension thereof;

b) at least one water-soluble or water-dispersible long chain aliphatic hydrocarbyl dimethyl amine oxide in which the hydrocarbyl group is a linear or substantially linear saturated or olefinically unsaturated aliphatic group having in the range of about 8 to about 22 carbon atoms, or a solution or suspension thereof;

c) at least one water-soluble or water-dispersible polyethoxylated monohydric saturated or olefinically-unsaturated alcohol of the formula:

RO—[CH$_2$CH$_2$O]$_n$H in which R has at least about 8 carbon atoms and is a straight or branched chain saturated aliphatic hydrocarbyl group or a straight or branched chain monoolefinically or a poly-olefinically unsaturated hydrocarbyl group having from 1 to 3 olefinic double bonds, and in which n is in the range of about 2 to about 50, or a solution or suspension thereof; and d) at least one water-soluble or water-dispersible N-hydrocarbyl pyridinium halide having up to about 24 carbon atoms in the molecule, and wherein (i) the hydrocarbyl group attached to the nitrogen atom of the heterocyclic aromatic ring of the pyridinium nucleus is a saturated or olefinically unsaturated aliphatic hydrocarbyl group having the range of about 4 to about 18 carbon atoms, and (ii) the ring carbon atoms of the pyridinium nucleus itself are either unsubstituted or one or more of such ring carbon atoms are substituted with a short chain alkyl group of up to about 4 carbon atoms, or a solution or suspension thereof.

24. A method according to claim 23 wherein said ingredient a) before it is mixed with the water or with any other ingredient used in forming said composition is an amine or alkylsulfonium salt of glyphosate or a solution or suspension thereof.

25. A method according to claim 23 wherein said ingredient a) before it is mixed with the water or with any other ingredient used in forming said composition is the isopropyl amine salt of glyphosate or a solution or suspension thereof.

26. A method according to claim 23 wherein ingredient a) is the only herbicide used in forming said composition.

27. A method according to claim 23 wherein said ingredient b) before it is mixed with the water or with any other ingredient used in forming said composition is one or more alkyl dimethyl amine oxides in which the alkyl group contains about 8 to about 16 carbon atoms, or a solution of suspension thereof; wherein said ingredient c) before it is mixed with the water or with any other ingredient used in forming said composition is one or more polyethoxylated saturated straight chain aliphatic alcohols in which the hydrocarbyl group has in the range of about 10 to about 20 carbon atoms, and in which there is an average in the range of about 5 to about 20 ethyleneoxy groups in the molecule, or a solution or suspension thereof; and wherein said, ingredient d) before it is mixed with the water or with any other ingredient used in forming said composition is one or more N-alkyl pyridinium chlorides or bromides in which the N-alkyl group his in the range of about 10 to about 18 carbon atoms and in which the ring carbon atoms of the pyridinium nucleus itself are unsubstituted, or a solution or suspension thereof.

28. A method according to claim 23 wherein said ingredient a) before it is mixed with the water or with any other ingredient used in forming said composition is one or more amine or alkylsulfonium salts of glyphosate, or a solution or suspension thereof; wherein said ingredient b) before it is mixed with the water or with any other ingredient used in forming said composition is one or more alkyl dimethyl amine oxides in which the alkyl group contains in the range of about 12 to about 16 carbon atoms, or a solution or suspension thereof; wherein said ingredient c) before it is mixed with the water or with any other ingredient used in forming said composition is a mixture of lauryl and myristyl alcohol ethoxylates having an average in the range of about 6 to about 12 ethyleneoxy groups per molecule, or a solution or suspension thereof; and wherein said ingredient d) before it is mixed with the water or with any other ingredient used in forming said composition is one or more N-alkyl pyridinium chlorides or bromides in which the alkyl group is an n-alkyl group having in the range of about 10 to about 16 carbon atoms, or a solution or suspension thereof.

29. A method according to claim 28 wherein said ingredient a) before it is mixed with the water or with any other ingredient used in forming said composition is the isopropyl amine salt of glyphosate, or a solution or suspension thereof.

30. A method according to claim 23 wherein ingredient b) is tetradecyldimethylamine oxide, ingredient c) is a mixture of ethoxylated lauryl, myristic and cetyl alcohols with an average of about 9 ethylene oxide units per molecule, and ingredient d) is N-dodecylpyridinium bromide.

31. A method of controlling vegetation which comprises applying to plant foliage a herbicidal or plant growth regulant amount of a herbicide or plant growth regulant composition containing only the elements C, H, O, N, P, and Cl or Br, and optionally S, and formed from the following ingredients:

a) at least one agriculturally acceptable salt of glyphosate, or a solution or suspension thereof;

b) at least one water-soluble or water-dispersible long chain aliphatic hydrocarbyl dimethyl amine oxide in which the hydrocarbyl group is a linear or substantially linear saturated or olefinically unsaturated aliphatic group having in the range of about 8 to about 22 carbon atoms, or a solution or suspension thereof;

c) at least one water-soluble or water-dispersible polyethoxylated monohydric saturated or olefinically-unsaturated alcohol of the formula:

in which R has at least about 8 carbon atoms and is a straight or branched chain saturated aliphatic hydrocarbyl group or a straight or branched chain monoolefinically or a poly-olefinically unsaturated hydrocarbyl group having from 1 to 3 olefinic double bonds, and in which n is in the range of about 2 to about 50, or a solution or suspension thereof; and d) at least one water-soluble or water-dispersible N-hydrocarbyl pyridinium halide having up to about 24 carbon atoms in the molecule, and wherein (i) the hydrocarbyl group attached to the nitrogen atom of the heterocyclic aromatic ring of the pyridinium nucleus is a saturated or olefinically unsaturated aliphatic hydrocarbyl group having in the range of about 4 to about 18 carbon atoms, and (ii) the ring carbon atoms of the pyridinium nucleus itself are either unsubstituted or one or more of such ring carbon atoms are substituted with a short chain alkyl group of up to about 4 carbon atoms, or a solution or suspension thereof;

ingredient a) being the only herbicide or plant growth regulant used in forming said composition, and ingredients b), c) and d) being the only surfactants used in forming said composition; and e) optionally, one or more agriculturally acceptable substances none of which is a herbicide, or a plant growth regulant or a surfactant.

32. A method according to claim 31 wherein said herbicide or plant growth regulant composition is a water solution, and wherein said composition is applied to the foliage by spraying the water solution onto the foliage.

33. A method according to claim 31 wherein said herbicide or plant growth regulant composition is in the form of a powder, and wherein said composition is applied to the foliage as a foliar dust.

34. A method according to claim 31 wherein ingredient a) is an amine, ammonium, alkali metal, alkylsulfonium, alkylphosphonium, sulfonylamine, and/or aminoguanidine salt of glyphosate.

35. A method according to claim 31 wherein ingredient b) is tetradecyldimethylamine oxide, ingredient c) is a mixture of ethoxylated lauryl, myristic and cetyl alcohols with an average of about 9 ethylene oxide units per molecule, and ingredient d) is N-dodecylpyridinium bromide.

* * * * *